United States Patent [19]

Bowles

[11] Patent Number: 5,206,366

[45] Date of Patent: Apr. 27, 1993

[54] PROCESS FOR PREPARING ARYL PIPERAZINYL-HETEROCYCLIC COMPOUNDS

[75] Inventor: Paul Bowles, Groton, Conn.

[73] Assignee: Pfizer Inc., New York, N.Y.

[21] Appl. No.: 936,179

[22] Filed: Aug. 26, 1992

[51] Int. Cl.$^5$ .................. C07D 417/06; C07D 413/06
[52] U.S. Cl. .................. 544/368; 544/230; 544/284; 544/363; 544/366; 544/373; 544/376
[58] Field of Search .............. 544/230, 284, 363, 368, 544/366, 373, 376

[56] References Cited

U.S. PATENT DOCUMENTS

| 4,558,060 | 12/1985 | Caignard et al. | 514/375 |
| 4,610,988 | 9/1986 | Davis et al. | 544/368 |
| 4,831,031 | 5/1989 | Lowe, III et al. | 544/368 |
| 4,883,795 | 11/1989 | Lowe, III et al. | 544/368 |

*Primary Examiner*—Cecilia Tsang
*Attorney, Agent, or Firm*—Peter C. Richardson; Paul H. Ginsburg; Valerie M. Fedowich

[57] ABSTRACT

A process for preparing a compounds of the formula

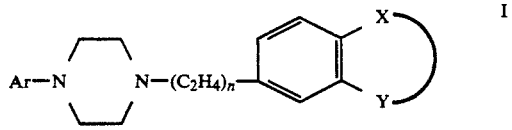

or a pharmaceutically acceptable acid addition salt thereof, which comprises reacting a monosubstituted piperazine of the formula

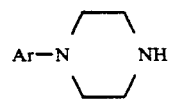

with an alkyl halide containing compound of the formula

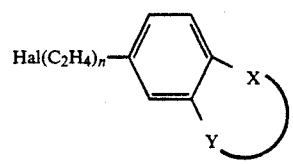

in water with a reagent to neutralize the hydrohalic acid and refluxing the mixture under conditions which are suitable to effect the coupling of said monosubstituted piperazines with said alkyl halide containing compound.

16 Claims, No Drawings

PROCESS FOR PREPARING ARYL PIPERAZINYL-HETEROCYCLIC COMPOUNDS

BACKGROUND OF THE INVENTION

The present invention is directed to a novel process for preparing arylpiperazinyl-ethyl(or butyl)-heterocyclic compounds and their pharmaceutically acceptable acid addition salts.

U.S. Pat. No. 4,831,031, the disclosure of which is hereby incorporated herein by reference, indicates that arylpiperazinyl-ethyl(or butyl)-heterocyclic compounds may be prepared by reacting piperazines of the formula II with compounds of the formula III as follows:

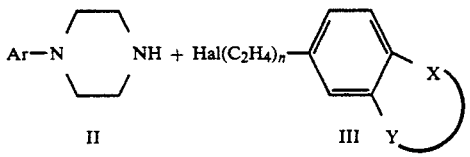

Wherein Hal is fluoro, chloro, bromo or iodo; and Ar, n, X and Y are as defined therein with reference to formula I. The '031 patent indicates that this coupling reaction is generally conducted in a polar solvent, such as a lower alcohol, dimethylformamide or methylisobutylketone, and in the presence of a weak base and that, preferably, the reaction is in the further presence of a catalytic amount of sodium iodide, and a neutralizing agent for hydrochloride such as sodium carbonate.

The present invention relates to a new and useful process for effecting coupling reactions of piperazine derivatives with alkyl halide derivatives that provide aryl piperazinyl-ethyl (or butyl)-heterocyclic compounds in greater yields than known methods. In the present invention, the coupling reaction is conducted in water. This aqueous process has not shown formation of byproducts in contrast to previous methods which produce undesirable byproducts and require special isolation procedures, i.e., extractions, distillations and recrystallizations.

SUMMARY OF THE INVENTION

The present invention relates to a novel process of preparing compounds of the formula

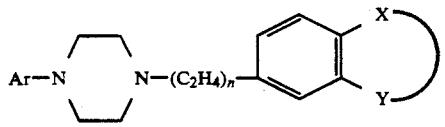

and the pharmaceutically acceptable acid addition salts thereof wherein Ar is naphthyl optionally substituted by fluoro, chloro, trifluoromethyl, methoxy, cyano or nitro; quinolyl; isoquinolyl; 6-hydroxy-8-quinolyl; benzoisothiazolyl or an oxide or dioxide thereof, each optionally substituted by fluoro, chloro, trifluoromethyl, methoxy, cyano, or nitro; benzothiazolyl; benzothiadiazolyl; benzotriazolyl; benzoxazolyl; benzoxazolonyl; indolyl; indanyl optionally substituted by one or two fluoro; 3-indazolyl optionally substituted by 1-trifluoromethylphenyl; or phthalazinyl; n is 1 or 2; and X and Y together with the phenyl to which they are attached form quinolyl; 2-hydroxyquinolyl; benzothiazolyl; 2-aminobenzothiazolyl; benzoisothiazolyl; indazolyl; 3-hydroxyindazolyl; indolyl; spiro[cyclopentane-1,3'-indolinyl]; oxindolyl; optionally substituted by one to three of $(C_1-C_3)$ alkyl, or one of chloro, fluoro or phenyl, said phenyl optionally substituted by one chloro or fluoro; benzoxazolyl; 2-aminobenzoxazolyl; benzoxazolonyl; 2-aminobenzoxazolinyl; benzothiazolonyl; benzoimidazolonyl; or benzotriazolyl; which comprises reacting a monosubstituted piperazine of the formula

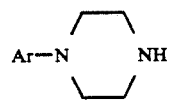

wherein Ar is as defined above, with an alkyl halide containing compound of the formula

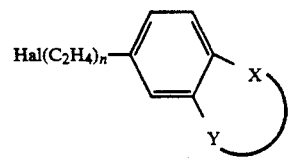

wherein n, X and Y are as defined above and Hal is fluoro, chloro, bromo or iodo, in water with a reagent to neutralize the hydrohalic acid and refluxing the mixture under conditions which are suitable to effect the coupling of said monosubstituted piperazines with said alkyl halide containing compound, and, if desired, preparing the corresponding pharmaceutically acceptable acid addition salt.

Both the monosubstituted piperazines and the alkyl halide containing compounds are referred to herein as substrates. For the purposes of the present invention, the substrates can be present in equal molar amounts or one substrate can be present in excess.

The optional substitution in the naphthyl and oxindolyl may be in either ring of the naphthyl and oxindolyl group, respectively. Examples of such substitutions are 6-fluoronaphthyl, 4-methoxynaphthyl, 1-ethyloxindolyl and 6-fluorooxindolyl. The optional substitution in the indanyl is in the saturated ring of the indanyl group. Specific substitution of the oxindolyl by $(C_1-C_3)$ alkyl is by one to three methyl groups, or one ethyl. The optional substitution in the phenyl is for instance at the 3-position.

Preferred compounds for use in the process of the present invention are those wherein n is 1, those wherein X and Y together with the phenyl to which they are attached form oxindolyl and those wherein Ar is naphthyl or benzoisothiazolyl.

A specific preferred compound which may be prepared in accordance with the present invention is 5-(2-(4-(1,2-benzisothiazol-3-yl)-1-piperazinyl)ethyl-6 -chloro-1,3-dihydro-2H-indol-2-one hydrochloride

DETAILED DESCRIPTION OF THE INVENTION

Generally, the process of the invention is effected in the presence of a neutralizing agent, for example, a base and including but not limited to alkali or alkaline earth metal carbonates such as, sodium carbonate or potassium carbonate; bicarbonates, such as, sodium bicarbonate; hydrides and tertiary amines such as, triethylamine or diisopropylethylamine.

In a preferred embodiment, the process of this invention involves the use of from about one to five molar equivalents of a neutralizing agent based on the substrate not present in excess with from about three to ten volumes of water based on the weight, e.g. grams, of the substrate not present in excess.

In a more preferred embodiment, the process of this invention involves the use of about two molar equivalents of a neutralizing agent based on the substrate with about five volumes of water based on the weight, e.g. grams, of the substrate which is not present in excess.

In a further preferred embodiment, the neutralizing agent is sodium carbonate.

The piperazine derivative and alkyl halide derivative form a substantially or totally insoluble mixture in water. After the materials are combined they are heated to reflux and refluxed for a time sufficient to allow the reaction to proceed, generally at least about 8 to 12 hours, and preferably for at least 10 to 12 hours. The reaction is preferably conducted at the reflux temperature of the reaction mixture including solvent, generally about 100° C. The flask is cooled generally to about room temperature (20°-25° C.) or below but not to freezing and the product is filtered off. This reaction has not shown formation of byproducts, in contrast to previous methods which produce undesirable byproducts and require special isolation procedures; i.e., extractions, distillations and recrystallizations.

The pharmaceutically acceptable acid addition salts of the compounds of formula I are prepared in a conventional manner by treating a solution or suspension of the free base (I) with about one chemical equivalent of a pharmaceutically acceptable acid. Conventional concentration and recrystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic, such as methanesulfonic, benzenesulfonic, and related acids.

The neuroleptic activity of the compounds prepared by the process of this invention makes them useful for treating psychotic disorders in human subjects. For example, these compounds are useful for treating psychotic disorders of the schizophrenic types, and in particular the compounds are useful for removing or ameliorating such symptoms as anxiety, agitation, excessive aggression, tension, and social or emotional withdrawal in psychotic patients.

A neuroleptic compound of formula I, or a pharmaceutically-acceptable salt thereof, (hereafter, also referred to as the active compounds), can be administered to a human subject either alone, or, preferably, in combination with pharmaceutically-acceptable carriers or diluents, in a pharmaceutical composition, according to standard pharmaceutical practice. A compound can be administered orally or parenterally. Parenteral administration includes especially intravenous and intramuscular administration. Additionally, in a pharmaceutical composition comprising an active compound the weight ratio of active ingredient to carrier will normally be in the range from 1:6 to 2:1, and preferably 1:4 to 1:1. However, in any given case, the ratio chosen will depend on such factors as the solubility of the active component, the dosage contemplated and the precise route of administration.

For oral use of an active compound the compound can be administered, for example, in the form of tablets or capsules, or as an aqueous solution or suspension. In the case of tablets for oral use, carriers which can be used include lactose and corn starch, and lubricating agents, such as magnesium stearate, can be added. For oral administration in capsule form, useful diluents are lactose and dried corn starch. When aqueous suspensions are required for oral use, the active ingredient can be combined with emulsifying and suspending agents. If desired, certain sweetening and/or flavoring agents can be added. For intramuscular and intravenous use, sterile solutions of the active ingredient can be prepared, and the pH of the solutions should be suitably adjusted and buffered. For intravenous use, the total concentration of solutes should be controlled to render the preparation isotonic.

When an active compound is to be used in a human subject to treat a psychotic disorder, the daily dosage will normally be determined by the prescribing physician. Moreover, the dosage will vary according to the age, weight and response of the individual patient as well as the severity of the patient's symptoms. However, in most instances, an effective amount for treating a psychotic disorder will be a daily dosage in the range from 5 to 500 mg, and preferably 50 to 100 mg, in single or divided doses, orally or parenterally. In some instances it may be necessary to use dosages outside these limits.

The following example is provided solely for the purpose of further illustration.

EXAMPLE 1

5-(2-(4-(1,2-benzisothiazol-3-yl)-1-piperazinyl)ethyl)-6-chloro-1,3-dihydro-2H-indol-2-one hydrochloride In a clean 12 liter 3 necked round bottom flask there were placed 500 grams (2.28 moles) of 3-piperazinyl-1,2-benzisothiazole; 525 grams (2.28 moles) of 2-chloroethyl-6-chlorooxindole; 535 grams (5.05 moles) of sodium carbonate and 2.54 liters of water.

The materials were combined and refluxed at 100° Centigrade overnight i.e., for at least about 9 to 12 hours. (Due to the fact that this mixture bubbles up after 4 hours at reflux, adequate head space is required.)

After approximately 16 hours the flask at reflux was cooled to room temperature i.e., generally from about 20°-25° C. and the mixture was stirred for approximately one hour and then filtered.

863 grams of a tan colored free base was recovered (91% weight yield). High pressure liquid chromatography (HPLC) shows this product to be 94.5% pure without purification. This free base product was characterized by proton NMR, thin layer chromatography, and melting point, i.e., m.p. 218°-220° C.

The free base was then converted to the hydrochloride salt and isolated in 86% weight yield and was characterized by proton NMR, thin layer chromatography, low resolution mass spectroscopy, high pressure liquid chromatography and melting point, i.e., m.p. >300° C.; MS (%): 488(1), 256(4), 232(100), 177(15); Analysis for $C_{21}H_{21}ClN_4OS \cdot HCl \cdot H_2O$: C 52.50, H 4.71, N 11.39. Found C 52.83, H 4.93, N 11.42. This product was 99.5% pure compared to the analytical standard.

I claim:

1. A process for preparing a compound of the formula:

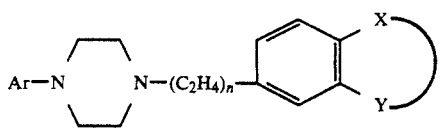

or a pharmaceutically acceptable acid addition salt thereof, wherein

Ar is naphthyl optionally substituted by fluoro, chloro, trifluoromethyl, methoxy, cyano or nitro; quinolyl; 6-hydroxy-8-quinolyl; isoquinolyl; quinazolyl; benzoisothiazolyl or an oxide or dioxide thereof, each optionally substituted by fluoro, chloro, trifluoromethyl, methoxy, cyano, or nitro; benzothiazolyl; benzothiadiazolyl; benzotriazolyl; benzoxazolyl; benzoxazolonyl; indolyl; indanyl optionally substituted by one or two fluoro; 3-indazolyl optionally substituted by 1-trifluoromethylphenyl; or phthalazinyl;

n is 1 or 2; and

X and Y together with the phenyl to which they are attached form quinolyl; 2-hydroxyquinolyl; benzothiazolyl; 2-aminobenzothiazolyl; benzoisothiazolyl; indazolyl; 2-hydroxyindazolyl; indolyl; spiro[cyclopentane-1,3'-indolinyl-indolinyl]; oxindolyl optionally substituted by one to three of $(C_1-C_3)$alkyl, or one of chloro, fluoro or phenyl, said phenyl optionally substituted by one chloro or fluoro; benzoxazolyl; 2-aminobenzoxazolyl; benzoxazolonyl; 2-aminobenzoxazolinyl; benzothiazolonyl; benzoimidazolonyl; or benzotriazolyl;

which comprises reacting a monosubstituted piperazine of the formula

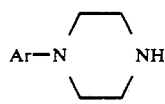

wherein AR is as defined above, with an alkyl halide containing compound of the formula

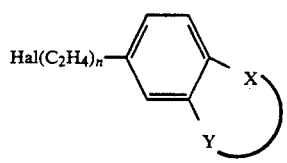

wherein n, X and Y are as defined above and Hal is fluoro, chloro, bromo or iodo, in water with a reagent to neutralize the hydrohalic acid and refluxing the mixture under conditions which are suitable to effect the coupling of said monosubstituted piperazines with said alkyl halide containing compound and, if desired, preparing the corresponding pharmaceutically acceptable acid addition salt.

2. A process according to claim 1 wherein the coupling of the monosubstituted piperazine with the alkyl halide containing compound is effected in the presence of a neutralizing agent.

3. A process according to claim 2 wherein from about one to five molar equivalents of a neutralizing agent based on the substrate not present in excess is used with from about three to ten volumes of water based on the weight of the substrate not present in excess.

4. A process according to claim 3 wherein about two molar equivalents of a neutralizing agent and about five volumes of water are used.

5. A process according to claim 4 wherein the neutralizing agent is selected from the group consisting of alkali metal carbonates, alkaline earth metal carbonates, bicarbonates, hydrides and tertiary amines.

6. A process according to claim 5 wherein the neutralizing agent is sodium carbonate.

7. A process according to claim 6 wherein the piperazine, alkyl halide containing compound, sodium carbonate and water are combined and heated to reflux.

8. A process according to claim 7 wherein the temperature of reflux is about 100° C.

9. A process according to claim 1 wherein the compound of the formula I is 5-(2-(4-(1,2-benzisothiazol-3-yl)-1-piperazinyl)ethyl)-6-chloro-1,3-dihydro-2-H-indol-2-one hydrochloride.

10. A process according to claim 1 which comprises reacting the monosubstituted piperazine with the alkyl halide containing compound in water and a neutralizing agent; refluxing the mixture for at least about 8 to 12 hours; cooling the mixture and filtering off the product.

11. A process according to claim 10 wherein from about one to five molar equivalents of a neutralizing agent based on the substrate not present in excess is used with from abut three to ten volumes of water based on the weight of the substrate not present in excess.

12. A process according to claim 11 wherein about two molar equivalents of a neutralizing agent and about five volumes of water are used.

13. A process according to claim 12 wherein the neutralizing agent is sodium carbonate.

14. A process according to claim 13 wherein the piperazine, alkyl halide containing compound, sodium carbonate and water are combined and heated to reflux.

15. A process according to claim 14 wherein the temperature of reflux is about 100° C.

16. A process according to claim 10 wherein the compound of formula I is 5-(2-(4-(1,2-benzisothiazol-3-yl)-1-piperazinyl)ethyl)-6-chloro-1,3-dihydro-2H-indol-2-one hydrochloride.

* * * * *